(12) United States Patent
Haddad et al.

(10) Patent No.: US 8,658,557 B2
(45) Date of Patent: Feb. 25, 2014

(54) CATALYST FOR N-BUTANE OXIDATION TO MALEIC ANHYDRIDE

(75) Inventors: Muin S. Haddad, Naperville, IL (US); Robert A. Gustaferro, Naperville, IL (US)

(73) Assignee: INEOS USA LLC, Lisle, IL (US)

( * ) Notice: Subject to any disclaimer, the term of this patent is extended or adjusted under 35 U.S.C. 154(b) by 133 days.

(21) Appl. No.: 13/317,656

(22) Filed: Oct. 25, 2011

(65) Prior Publication Data

US 2013/0102455 A1    Apr. 25, 2013

(51) Int. Cl.
| | |
|---|---|
| B01J 20/34 | (2006.01) |
| B01J 27/00 | (2006.01) |
| B01J 27/198 | (2006.01) |
| B01J 27/19 | (2006.01) |
| B01J 27/185 | (2006.01) |

(52) U.S. Cl.
USPC ............... 502/209; 502/20; 502/31; 502/208; 502/211; 502/213

(58) Field of Classification Search
USPC ....................... 502/20, 31, 208, 209, 211, 213
See application file for complete search history.

(56) References Cited

U.S. PATENT DOCUMENTS

| | | | | |
|---|---|---|---|---|
| 3,255,211 | A * | 6/1966 | Kerr ............................. | 260/346.8 |
| 4,147,661 | A * | 4/1979 | Higgins et al. ................ | 252/435 |
| 5,021,384 | A * | 6/1991 | Hatano et al. ................. | 502/209 |
| 5,364,824 | A * | 11/1994 | Andrews et al. .............. | 502/209 |
| 5,480,853 | A * | 1/1996 | Bortinger ...................... | 502/224 |
| 5,945,368 | A * | 8/1999 | Felthouse et al. ............. | 502/209 |
| 7,638,457 | B2 * | 12/2009 | Ghelfi et al. ................... | 502/209 |
| 8,143,461 | B2 * | 3/2012 | Forkner ......................... | 568/956 |
| 8,404,614 | B2 * | 3/2013 | Shan .............................. | 502/208 |

FOREIGN PATENT DOCUMENTS

| | | | | |
|---|---|---|---|---|
| DE | 198 25 389 | * 12/1999 | ............. | B01J 27/198 |
| WO | 2013/062919 | * 5/2013 | ............... | B01J 35/00 |

OTHER PUBLICATIONS

"Vanadyl hydrogenphosphate sesquihydrate as a precursor for preparation of (VO)2P2O7 and cobalt-incorporated catalysts," Tomohiro Ishimura et al. Journal of Molecular Catalysis A: Chemical 158 (2000), pp. 559-565.*

* cited by examiner

*Primary Examiner* — Patricia L Hailey
(74) *Attorney, Agent, or Firm* — David P. Yusko; INEOS USA LLC

(57) ABSTRACT

A process for the preparation of a promoted VPO catalyst, wherein the catalyst comprises the mixed oxides of vanadium and phosphorus and wherein the catalyst is promoted with at least one of niobium, cobalt, iron, zinc, molybdenum or titanium, said process comprising the steps of
  (i) preparing a VPO catalyst comprising vanadyl pyrophosphate as the major component and containing less than 5 wt % of vanadyl phosphate,
  (ii) contacting the VPO catalyst with a solution comprising a metal source compound of at least one metal selected from the group consisting of niobium, cobalt, iron, zinc, molybdenum or titanium to form a metal impregnated VPO catalyst, and
  (iii) drying the metal impregnated VPO catalyst to form the promoted VPO catalyst.

In one embodiment, a niobium promoted VPO catalyst is prepared.

17 Claims, No Drawings

CATALYST FOR N-BUTANE OXIDATION TO MALEIC ANHYDRIDE

BACKGROUND OF THE INVENTION

1. Field of the Invention

The present invention relates to an improved catalyst for use in the oxidation of n-butane to maleic anhydride. In particular, the present invention is directed to the method of making metal promoted oxidation catalysts comprising the mixed oxides of vanadium and phosphorus, wherein the catalysts are promoted with at least one of niobium, cobalt, iron, zinc, molybdenum or titanium. This preparation method yields improved catalytic compositions for the oxidation of n-butane to maleic anhydride.

2. Description of the Prior Art

Maleic anhydride is a well known and versatile intermediate for the manufacture of unsaturated polyester resins, chemical intermediates such as butanediol and tetrahydrofuran, pharmaceuticals and agrochemicals. It is produced by partial oxidation of aromatic (e.g., benzene) or non-aromatic (e.g., n-butane) hydrocarbons. The oxidation is performed in the gas phase, in the presence of a heterogeneous catalyst. The oxidation reaction may be carried out in a fixed, fluidized, or riser bed reactor.

Catalysts containing vanadium and phosphorus oxides have been used in the oxidation of 4-carbon atom hydrocarbons, such as n-butane, n-butenes, 1,3-butadiene or mixtures thereof with molecular oxygen or oxygen-containing gas to produce maleic anhydride. Conventional methods of preparing these catalysts involve reducing a pentavalent vanadium compound, and combining the same with a phosphorus compound, and if desired, promoter element compounds under conditions which will provide vanadium in a valence state below +5 to form catalyst precursors capable of being converted to vanadium phosphorus oxide. The catalyst oxide precursor is then recovered and converted to active catalytic material before or after the suitable catalyst particles for either fixed bed or fluid bed are formed.

The prior art describes many different procedures for this preparation, which in general involve the use of vanadium pentoxide ($V_2O_5$) as a source of vanadium (see e.g. U.S. Pat. No. 5,137,860 and EP 0 804 963 A1). Hydrogen chloride in aqueous solution is one of the reducing agents mentioned for the reduction of $V^{+5}$ to $V^{+4}$. Also used are organic reducing media like primary or secondary aliphatic alcohols or aromatic alcohols such as isobutyl alcohol and benzyl alcohol. The most used organic reducing agent is isobutyl alcohol since it combines optimal solvent and redox characteristics, thus favouring a complete redox reaction with formation of tetravalent vanadium, which is reacted with phosphoric acid to form vanadyl acid orthophosphate hemihydrate, (VO)$HPO_4$.$0.5H_2O$, which is then subject to further heat treatment to yield a finished catalyst.

U.S. Pat. Nos. 3,888,886; 3,905,914; 3,931,046; 3,932,305 and 3,975,300 disclose the testing of promoted vanadium phosphorus oxide catalysts for maleic anhydride production from butane in one inch diameter fluid bed reactors. In most instances, the catalysts were prepared by forming the vanadyl acid orthophosphate hemihydrate catalyst precursor in aqueous media (in U.S. Pat. No. 3,975,300 the precursor was formed in a paste of a vanadium compound, a phosphorus compound and an organic reducing agent), drying and thereafter grinding and sieving the precursor to a powder of about 74 to 250 microns size.

U.S. Pat. No. 4,647,673 discloses a process for the preparation of attrition resistant, microspheroidal fluid bed catalysts comprising the mixed oxides of vanadium and phosphorus in which a vanadium phosphorus mixed oxide catalyst precursor is densified, comminuted, formed into fluidizable particles and calcined under fluidization-type conditions.

The performance of catalyst comprising the mixed oxides of vanadium and phosphorus may be modified and can be substantially improved by the addition of a promoter element selected from the groups IA, IB, IIA, IIB, IIIA, IIIB, IVA, IVB, VA, VB, VIA, VIB and VIIIA of the periodic table of elements, or of mixtures of such elements. Patent literature claims that the catalytic performance of such catalyst can be substantially improved by addition of these elements. A review of the promoters reported in the literature and of their role has been reported by G. J. Hutchings in Appl. Catal., 1991, 72, 1-32, and in Stud. Surf. Sci. Catal. "Preparation of Catalysts VI", (G. Poncelet et al., Eds.), Vol. 91, Elsevier Science, Amsterdam, 1995, p. 1. Other mention of promoters to improve the performance of catalyst comprising the mixed oxides of vanadium and phosphorus include V. Guliants et al. (Catalyst Letters 62 (1999), 87-9) wherein such catalysts were promoted with Nb, Si, Ti, and Zr; I. Mastuura, et al. (Catal. Today, 1996, 28, 133-138) wherein co-precipitate V and Nb are co-precipitated in an aqueous solution and then the precipitate is treated with benzyl alcohol at reflux; P. G. Pries de Oliveira, et al. (Catal. Today, 2000, 57, 177-186) wherein the VPO precursor is prepared in isobutyl alcohol and $NbPO_4$ is introduced just before the nucleation of vanadyl acid orthophosphate hemihydrate; A. M. Duarte de Farias et al. (J. Catal. 2002, 208, 238-246) solubilize Nb ethoxide into isobutyl alcohol and use it as a reducing agent to prepare the Nb modified catalyst precursor and then the precursor is activated under reaction conditions; U.S. Pat. No. 4,147,661 to Higgins et al. wherein the Nb promoted catalyst is prepared in isobutyl alcohol using hydrogen chloride gas as reducing agent; U.S. Pat. No. 7,638,457 to Ghelfi et. al, wherein small amounts of Nb compounds or salts thereof are added in the preparation of a catalyst precursor mixture, which mixture includes a vanadium source, a phosphorus source, an organic medium capable of acting as a solvent and a reducing agent, and an additive selected from the group consisting of benzyl alcohol and polyols, followed by a thermal treatment of the precursor carried out in the presence of steam.

SUMMARY OF THE INVENTION

The present invention is directed a process for the preparation of an improved promoted oxidation catalyst comprising the mixed oxides of vanadium and phosphorus for the oxidation of n-butane to maleic anhydride, wherein the catalyst is promoted with at least one of niobium, cobalt, iron, zinc, molybdenum or titanium. These improved catalysts, prepared as described herein, provides greater overall conversion of n-butane to maleic anhydride than promoted catalyst prepared by prior art preparations.

In one embodiment, the invention is a process for the preparation of a promoted VPO catalyst, wherein the catalyst comprises the mixed oxides of vanadium and phosphorus and wherein the catalyst is promoted with at least one of niobium, cobalt, iron, zinc, molybdenum or titanium, said process comprising the steps of (i) preparing a VPO catalyst comprising vanadyl pyrophosphate as the major component and containing less than 5 wt % of vanadyl phosphate, (ii) contacting the VPO catalyst with a solution comprising a metal source compound of at least one metal selected from the group consisting of niobium, cobalt, iron, zinc, molybdenum or titanium to form a metal impregnated VPO catalyst, and (iii) drying the metal impregnated VPO catalyst to form the promoted VPO catalyst.

In one embodiment, the invention is a process for the preparation of the niobium promoted oxidation catalyst comprises the steps of (i) preparing a VPO catalyst comprising vanadyl pyrophosphate as the major component and containing less than 5 wt % of vanadyl phosphate, (ii) contacting the VPO catalyst with a niobium containing solution to form a niobium impregnated VPO catalyst, and (iii) drying the niobium impregnated VPO catalyst to form the niobium promoted oxidation catalyst.

DETAILED DESCRIPTION OF THE INVENTION

The instant invention is a process for the preparation of an improved niobium promoted oxidation catalyst comprising the mixed oxides of vanadium and phosphorus for the oxidation of n-butane to maleic anhydride.

The Catalyst:

The catalyst of the instant invention comprises oxides of vanadium and phosphorus and is promoted with at least one of niobium, cobalt, iron, zinc, molybdenum or titanium.

Catalysts comprising vanadium, phosphorus and oxygen, hereinafter "VPO catalyst", are useful the oxidation of n-butane to maleic anhydride. Such catalyst typically comprise a mixture of the following phases: vanadyl pyrophosphate, $(VO)_2P_2O_7$; vanadyl metaphosphate $VO(PO_3)_2$ and vanadyl phosphate, $VOPO_4$.

Such multi-phase VPO catalysts are typically derived by the thermal treatment of vanadyl acid orthophosphate hemihydrate of the formula $(VO)HPO_4.0.5H_2O$, which may be prepared as described herein.

The improved promoted VPO catalysts of the instant invention, wherein the catalysts are promoted with at least one of niobium, cobalt, iron, zinc, molybdenum or titanium, are achieved by (i) preparing a VPO catalyst comprising vanadyl pyrophosphate as the major component and containing less than 5 wt % of vanadyl phosphate, (ii) contacting the VPO catalyst with a solution comprising a metal source compound of at least one metal selected from the group consisting of niobium, cobalt, iron, zinc, molybdenum or titanium to form a metal impregnated VPO catalyst, and (iii) drying the metal impregnated VPO catalyst to form the promoted VPO catalyst.

Typically, the amount of metal promoter in the resulting catalyst is between 0.1 and 1.0 wt %. In one embodiment, the molar ratio of the metal promoter to vanadium is between 0.0015 to 1 and 0.015 to 1. In another embodiment, the molar ratio of the metal promoter to vanadium is between 0.003 to 1 and 0.01 to 1.

VPO Catalyst Preparation:

A VPO catalyst containing the mixed oxides of vanadium and phosphorus, may be prepared by any method known in the art.

In one method for the preparation of an oxidation catalyst containing the mixed oxides of vanadium and phosphorus, a vanadium compound, particularly a pentavalent vanadium compound, is at least partially solubilized in an organic liquid medium. Suitable vanadium compounds containing pentavalent vanadium include: vanadium pentoxide or vanadium salts, such as ammonium metavanadate and vanadium oxytrihalides. Vanadium pentoxide is preferred. To aid in solubilizing the vanadium, it is preferred that the vanadium-containing compound which is introduced into the liquid medium have a small particle size, and methods for further reducing particle size of the vanadium compound while in the liquid medium, such as by ball milling the initial suspension of vanadium in the liquid medium, may be employed.

The liquid medium employed must be capable of reducing at least a portion of the vanadium to a +4 valence state, either upon addition and solvation, or upon mixing and heating. In addition the liquid medium should be a solvent for phosphoric acid and be relatively unreactive towards phosphoric acid. The liquid medium must not, however, be a solvent for the mixed oxide of vanadium and phosphorus. Suitable liquid media for use in the invention are organic compounds such as alcohols, aldehydes, ketones, ethers and mixtures of the above. The organic liquid media used in the invention is preferably anhydrous. Preferred organic liquids suitable for use as the liquid medium in this invention are alcohols, particularly isobutanol.

After the pentavalent vanadium compound is introduced into the liquid medium, reduction of the vanadium is effected, preferably by heating the resulting reaction medium, with stirring if desired. Preferred vanadium and phosphorus oxide catalysts for the oxidation of 4-carbon atom hydrocarbons to maleic anhydride contain vanadium in an average valence stage of about +3.9 to about +4.6. This average valence state is achieved when at least a portion of the pentavalent vanadium introduced into the reaction mixture is reduced to the +4 state, preferably about +4.1.

After at least partial reduction of the vanadium, a pentavalent phosphorus-containing compound is added to the reaction medium. Suitable phosphorus compounds containing pentavalent phosphorus include: phosphoric acid, phosphorus pentoxide, or phosphorus perhalide, such as phosphorus pentachloride. Phosphoric acid and phosphorus pentoxide are preferred. The pentavalent phosphorus-containing compound is preferably added to the reaction medium in the form of a solution of the phosphorus-containing compound in either a component of the liquid reaction medium, or in a liquid capable of yielding the phosphorus-containing compound to the liquid reaction medium. After addition of the phosphorus-containing compound to the liquid reaction medium, it is preferable to heat the liquid reaction medium with stirring, if necessary.

In the alternative, another method for the preparation of an oxidation catalyst containing the mixed oxides of vanadium and phosphorus, the phosphorus containing compound is added to the liquid medium followed by the addition of vanadium pentoxide to this mixture to form the reaction medium which is then heated with stirring.

As stated above, the liquid medium employed should not be a solvent for the vanadium-phosphorus mixed oxide. Therefore, as the vanadium-phosphorus oxide catalyst precursor is formed, it precipitates out of the liquid reaction medium. The total $H_2O$ content of the medium, particularly at this point, is typically below about 5%.

The catalyst precursor may be recovered from the liquid reaction medium in which it was prepared by conventional methods, such as evaporation, filtration, centrifugation, decanting, and the like. In one embodiment, the precursor is dried by heating. Alternatively, the recovered precursor, which is still partially wet with the organic liquid, may be treated with a low boiling solvent such as petroleum ether. In another embodiment, excess preparational reaction media may be substantially removed by vacuum filtration. In yet another embodiment, excess water can be introduced into the precursor containing organic liquid reaction medium, allowing an organic layer to separate from the aqueous layer followed by recovery of the catalyst precursor by drying.

After recovery, the catalyst precursor is subjected to densification and comminution. The order in which the catalyst precursor is densified and comminuted is dependent upon the method used for accomplishing these purposes. For example, the catalyst precursor may be densified by tableting or pelleting the catalyst precursor, and thereafter crushing or grinding the densified material to prepare it for formation of the microspheroidal particles. Alternatively, the catalyst precursor may be recovered by drying or spray drying, and thereafter subjected to dry ball milling in order to both densify the precursor material and comminute the catalyst precursor to an average particle size less than about 1 micron in diameter. The steps of densifying and comminuting the catalyst precursor may be repeated such that the final fluidizable catalyst particle has a bulk density equal to or greater than about 0.75 grams per cubic centimeter, preferably greater than or equal to 1 gram per cubic centimeter.

The densified, comminuted catalyst precursor is then formed into microspheroidal fluidizable particles. Formation may be accomplished by the oil drop method, in which an aqueous solution of the catalyst precursor is dropped into a hot oil bath to cause the formation of spheroidal particles. In another embodiment, the microspheroidal fluidizable particles are formed by spray drying an aqueous slurry of the catalyst precursor.

The formation of fluidizable particles by crushing and screening to form a fluidizable fraction is not suitable for forming attrition resistant catalysts, as the particles easily abraid during fluid bed operation due primarily to their irregular surface texture.

If spray drying is to be utilized, the catalyst precursor preferably should be uncalcined when introduced into water to form the aqueous slurry. Substantial contacting of the calcined vanadium phosphorus mixed oxide catalyst with water (at less than 100° C.) reduces the activity of the catalyst, particularly if calcined in air.

The solids content of the catalyst precursor containing aqueous slurry should be adjusted to about 25 to about 60 weight %. In one embodiment, the solids content is above about 40 weight %. The catalyst precursor-containing aqueous slurry is then spray dried to form uniform, microspheroidal particles having a particle size range of between about 20 to about 300 microns, generally between 20 to about 240 microns. Spray drying may be accomplished by methods known in the art.

The catalyst may comprise 100% active phase with no added inert diluents or supports. In other embodiments, inert diluents or supports may be added to the fluid bed catalyst by the addition of the diluent or support before or during any of the densification, comminution, and formation of the microspheroidal fluidizable particle steps. Such inert diluents or supports may include silica, alumina, alumina silica, titania, niobia, silicon carbide, and the like. In one embodiment the catalyst comprises at least 70% active material. In another embodiment the catalyst comprises at least 80% active material. In yet another embodiment, the catalyst comprises at least 90% active material.

The fluidizable particles prepared above are subjected to calcination under fluidization-type conditions. Fluidization conditions can be determined readily by those of skill in the art, and include the introduction of a gas stream into a catalyst containing fluid bed vessel sufficient to "raise" the catalyst bed and contact substantially all catalyst particles with the gaseous feed, maintaining isothermal temperature control. Other calcination techniques such as cascading calcination, which, similar to fluidization calcination, provide homogeneous gas contacting of the catalyst particles and relatively isothermal temperature control, may be utilized according to the present invention, to result in fluidization-type conditions sufficient to impart attrition resistance to the calcined catalyst. Fluid bed calcination is, however, preferred.

The catalyst is calcined in air or an oxygen containing gas under fluidization-type conditions at a temperature range of about 300° C. to about 450° C. The catalyst may be calcined additionally in the presence of hydrocarbon, an inert gas, or steam. In one embodiment, the calcination temperature is increased from about 300° C. to about 325° C., and then increased steadily to about 400° C. to about 425° C. In one embodiment, the temperature increase is at a rate of about 0.5° C. to 5° C. per minute. Calcination times vary depending upon method of preparation, catalyst composition and amount of catalyst, but generally calcination is conducted for a period of time greater than 1 hour.

The catalyst precursor may contain promoter elements, including but not limited to alkali metals, alkaline earth metals, Ti, Cr, W, Ta, U, Co, Mo, Fe, Zn, Hf, Zr, Mn, As, Sb, Te, Bi, Sn, Ge, Nb, Ni, Cu, Cd, Ce, rare earths or mixtures thereof. These may be incorporated into the catalyst precursor in any of the methods known in the art, such as inclusion via the liquid reaction medium prior to or after reduction of the vanadium, or during one or more steps of the preparation of the fluidizable catalyst. The promoter elements may be added to the catalyst as metals, oxides, hydroxides, carbonates, or salts such as halides, nitrates, acetates, formates, butyrates, benzylates, and the like. In one embodiment, the molar ratio of promoter elements to vanadium is 0.001:1 to 1:1, In another embodiment, the molar ratio of promoter elements to vanadium is 0.003:1 to 0.5:1.

Catalysts suitable for the production of maleic anhydride from 4-carbon atom hydrocarbons generally have a phosphorus to vanadium ratio of about 2:1 to about 0.5:1, preferably about 0.8:1 to about 1.3:1. Most preferred is a P/V ratio of about 1.2:1. These catalysts preferably exhibit an average valence for vanadium within the range of +3.5 to +4.6, preferably about +4.

Vanadyl Pyrophosphate Content

VPO catalyst prepared by prior art processes, including the preparation described above typically contains a mixture of the following phases: vanadyl pyrophosphate, $(VO)_2P_2O_7$; vanadyl metaphosphate $VO(PO_3)_2$ and vanadyl phosphate, $VOPO_4$. A key feature of the process of the instant invention is that the VPO catalyst comprise vanadyl pyrophosphate as the major component and contain less than 5 wt % of vanadyl phosphate.

If the vanadyl phosphate content of the VPO catalyst is greater than the desired range (i.e. greater than or equal to 5 wt % of vanadyl phosphate), it is possible to lessen the amount of vanadyl phosphate in the VPO catalyst by operating the catalyst under butane oxidation conditions to produce maleic anhydride for a period of time sufficient to achieve the desired levels of the vanadyl phosphate phase. In one embodiment, the vanadyl phosphate phase content of a VPO catalyst is reduced to an acceptable level or eliminated completely by operating the VPO catalyst under butane oxidation conditions for about 4 hours to about 80 hours. In another embodiment, the vanadyl phosphate phase may be lessened or removed from the VPO catalyst by "washing" the VPO catalyst with water. In one embodiment, the "washing" procedure comprises combining a solid VPO catalyst with water, removing the water and collecting the solid by filtration, and then drying the filtrate solid to achieve a VPO catalyst containing less or little (if any) of the vanadyl phosphate phase.

Impregnation with Metal Promoters

The process of the instant invention comprises promoting, via impregnation, the VPO catalyst comprising vanadyl pyrophosphate as the major component and containing less than 5 wt % of vanadyl phosphate, with at least one of niobium, cobalt, iron, zinc, molybdenum or titanium. In one embodiment VPO catalyst is promoted with niobium. In another embodiment, the VPO catalyst is promoted with cobalt. In another embodiment, the VPO catalyst is promoted with iron. In another embodiment, the VPO catalyst is promoted with zinc. In another embodiment, the VPO catalyst is promoted with molybdenum. Lastly, in another embodiment, the VPO catalyst is promoted with titanium.

This process comprises contacting the VPO catalyst with a solution comprising at least one metal source compound of at least one metal selected from the group consisting of niobium, cobalt, iron, zinc, molybdenum or titanium, in order to coat or impregnate the surface of the catalyst with the solution comprising the metal source compound. As used herein, a "source compound" is any compound containing at least one of the claimed promoter elements wherein the compound is at least partially soluble in an aqueous solvent or non-aqueous solvent to form a solution. Suitable source compounds of niobium, cobalt, iron, zinc, molybdenum or titanium include ammonium niobium oxalate, cobalt acetate, zinc acetate, phosphomolybdic acid, ferric ammonium citrate, and titanium (IV) bis(ammonium lactato)dihydroxide. For avoidance of doubt, ammonium niobium oxalate, generally represented by the formula $NH_4[NbO(C_2O_4)_2(H_2O)_2].(H_2O)$, may additionally include the following phases, $NH_4(HC_2O_4)(H_2C_2O_4).2(H_2O)$, $NH_4[NbO(C_2O_4)_2(H_2O)_2].3(H_2O)$, and $(NH_4)_3[NbO(C_2O_4)_3].(H_2O)$.

In one embodiment, microspheroidal particles of the VPO catalyst are contacted with the solution comprising the metal source compound. The solution comprising the metal source compound may comprise an aqueous solvent or a non-aqueous solvent or a mixture thereof. The solution comprising the metal source compound may comprise source compounds of more than one metal. In one embodiment, the solution comprising the metal source compound is between 5% and 20% by volume source compound and the remainder is water.

The contacting may be done by any incipient wetness impregnation technique or method known in the art, including immersion of the VPO catalyst in the solution comprising the metal source compound or spraying the solution comprising the metal source compound onto the VPO catalyst. When a VPO catalyst is contacted with the solution comprising the metal source compound, the solution is absorbed into the pores of the catalyst. After contacting the VPO catalyst is "wet" or "damp" with the solution comprising the metal source compound.

After contacting or impregnation with solution comprising the metal source compound, the wet VPO catalyst is dried to remove the organic or aqueous solvent employed in the solution comprising the metal source compound. The wet catalyst is dried by heating at an elevated temperature for a time sufficient to remove the solvent. In one embodiment the impregnated catalyst is dried in a nitrogen atmosphere. Typically, the wet VPO catalyst is dried at between 100° C. and 300° C. for between 2 hrs. and 5 hrs. In one embodiment the wet VPO catalyst is dried at about 200° C. for about 3 hrs.

In one embodiment, the VPO catalyst is contacted with a niobium containing solution. In one embodiment, the niobium containing solution is a 10% ammonium niobium oxalate in water solution. In another embodiment, the VPO catalyst is contacted with a cobalt containing solution. In another embodiment, the VPO catalyst is contacted with an iron containing solution. In another embodiment, VPO catalyst is contacted with a zinc containing solution. In another embodiment, the VPO catalyst is contacted with a molybdenum containing solution. Lastly, in another embodiment, the VPO catalyst is contacted with a titanium containing solution.

Oxidation of n-Butane to Maleic Anhydride:

The catalyst used in the present invention may be utilized in any type oxidation reactors known in the art. The catalyst may be formed into tablets, pellets or the like and employed in fixed bed reactors; or the catalyst may produced in small particle sizes of less than about 100 microns and be used in fluidized bed reactors.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. Preferred oxygen/hydrocarbon ratios in the reactor feed are about 4 to about 20 moles of oxygen per mole of hydrocarbon. The reaction temperature may vary widely and is dependent upon the particular hydrocarbon and catalyst employed. Generally, temperatures of about 325° C. to 500° C. are preferred, and temperatures from about 360° C. to about 460° C. are more preferred. The reaction may be conducted at atmospheric, superatmospheric or subatmospheric pressure, although operation at superatmospheric pressure is preferred. Generally, the feed contains about 0.2 to about 5.0 mole percent butane, preferably about 1.0 to about 4.0 mole percent butane, and the butane weight hourly space velocity (wwh) is about 0.005 to about 0.2 lbs butane per lb catalyst per hour, preferably about 0.01 to about 0.1 lbs butane per lb catalyst per hour. As used elsewhere herein, "butane oxidation conditions to produce of maleic anhydride" refers to the ranges of parameters set forth in this paragraph.

Additionally, it has been determined that by impregnating the VPO catalyst with an alkyl ester of orthophosphoric acid and adding the impregnated catalyst to a fluid bed VPO catalyst periodically, it is possible to add phosphorous to the VPO fluid bed catalyst and to achieve an increase in maleic anhydride yield at a lower operating temperature.

The preferred alkyl phosphate compound is an alkyl ester of orthophosphoric acid having the formula $(RO)_3P=O$ wherein each R is independently hydrogen or $C_1$ to $C_4$ alkyl, and at least one R is a $C_1$ to $C_4$. The more preferred phosphorus compounds are triethylphosphate or trimethylphosphate.

Generally the alkyl ester of orthophosphoric acid is added to the fluid bed catalyst in an amount of about 1 to about 25 parts by weight of alkyl ester of orthophosphoric acid per 100 parts by weight of the unenriched catalyst, preferably about 7 to about 23 parts by weight of alkyl ester of orthophosphoric acid per 100 parts by weight catalyst; more preferably about 8 to about 21 parts by weight of alkyl ester of orthophosphoric acid per 100 parts by weight catalyst, and more preferably about 16 to about 19 parts by weight of alkyl ester of orthophosphoric acid per 100 parts by weight catalyst.

Specific Embodiments

In order to illustrate the instant invention, catalyst prepared in accordance with the instant invention were evaluated and compared under similar reaction conditions to similar catalysts prepared by prior art methods outside the scope of the instant invention. The examples utilize a fluid bed reactor catalyst containing vanadium, phosphorus, and oxygen with a predominant phase of $(VO)_2P_2O_7$ and containing no promoter elements. The VPO catalyst employed in the examples is commercially available from INEOS USA LLC. All reactor testing of the promoted catalysts comprising the mixed oxides of vanadium and phosphorus was done in 1.5" pilot plant reactors containing 370 grams of catalyst, where test conditions were 30/1 air/butane ratio, 0.05 butane weight hourly space velocity (wwh), and 10 psig. Reactor temperature for each example is as listed in Table 1. All examples are provided for illustrative purposes only.

Example 1

Washing to Remove Vanadyl Phosphate

Grey-yellowish VPO catalyst powder containing 24.2% $VOPO_4$ was added to water in a weight ratio of 1 g catalyst/7.5 g water and stirred for 15 minutes. The slurry was then filtered under vacuum suction through a glass-fritted funnel. The filtrate was dark brown indicating significant removal of the $VOPO_4$ phase that imparted the yellowish coloration to the original powder. An additional 5 g of water/1 g of original catalyst were passed, under vacuum suction, over the collected solid. The collected solid was then dried in a drying oven at 120° C. for 2 hours. The dried catalyst weighed about 80% of its initial weight and looked dark grey without any yellow coloration. The x-ray diffraction pattern of the washed powder indicated no $VOPO_4$ phase presence.

Comparative Examples 2, 3 and 4

Samples of fresh (unused) VPO catalyst were tested under butane oxidation conditions. Butane conversion and maleic anhydride yield was as listed in Table 1.

Comparative Example 5

A used sample of VPO catalyst, that had previously been run under n-butane oxidation conditions to produce maleic anhydride, was tested in a 1.5" diameter steel fluidized bed reactor to determine maleic anhydride yield. The sample was tested under butane oxidation conditions. Butane conversion and maleic anhydride yield was as listed in Table 1.

Comparative Example 6

A fresh sample of niobium promoted VPO catalyst (prepared similarly to the other VPO catalyst used herein but with niobium added during the catalyst preparation) was tested in a 1.5" diameter steel fluidized bed reactor to determine maleic anhydride yield. The sample was tested at the conditions. Butane conversion and maleic anhydride yield was as listed in Table 1. Note that the yield is higher than for the catalysts in Comparative Examples 2-5.

Comparative Example 7

An ammonium niobium oxalate (ANO) in water solution containing 9.09 weight % ANO was added, with stirring, to fresh VPO catalyst in a weight ratio of 0.22 g solution/1 g catalyst. The VPO catalyst used in this example contained a relatively large amount (>8 weight %) of a minor phase, $VOPO_4$. The catalyst was dried in a laboratory oven at 120° C. for 2 hours. After drying, a portion of the sample was loaded to a 1.5" diameter steel fluidized bed reactor. The catalyst was fluidized with nitrogen and heated up to about 200° C. to decompose the oxalate and remove any residual water and then further heated to about 390° C. The catalyst was then tested under the n-butane oxidation conditions. Butane conversion and maleic anhydride yield was as listed in Table 1. Note that the yield is lower than that for the catalyst in Example 6 and also lower than that for catalysts in Comparative Examples 2-5.

Comparative Example 8

An ammonium niobium oxalate (ANO) in water solution containing 9.09 weight % ANO was added, with stirring, to fresh VPO catalyst in a weight ratio of 0.22 g solution/1 g catalyst. The VPO catalyst used in this example contained a relatively large amount (>24 weight %) of a minor phase, VOPO4. After the addition of the ANO solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated up to about 200° C. to decompose the oxalate and remove any residual water and then further heated to about 390° C. The catalyst was then tested under the n-butane oxidation conditions. Butane conversion and maleic anhydride yield was as listed in Table 1. Note that the yield is lower than that for the catalyst in Comparative Example 6 and also lower than that for catalysts in Comparative Examples 2-5

Example 9

An ammonium niobium oxalate (ANO) in water solution containing 9.09 weight % ANO was added, with stirring, to fresh VPO catalyst in a weight ratio of 0.22 g solution/1 g catalyst. The VPO catalyst used in this example contained only a very small amount (<2.5 weight %) of a minor phase, $VOPO_4$. After the addition of the ANO solution, the catalyst was dried in a laboratory oven at 120° C. for 4 hours. After drying, a portion of the sample was loaded to a 1.5" diameter steel fluidized bed reactor. The catalyst was fluidized with nitrogen and heated up to about 200° C. to decompose the oxalate and remove any residual water and then further heated to about 390° C. The catalyst was then tested under the n-butane oxidation conditions. Butane conversion and maleic anhydride yield was as listed in Table 1. Note that the yield is higher than those for the catalysts in Comparative Examples 2-5 and also higher than those for the catalyst in Example 6.

Example 10

An ammonium niobium oxalate (ANO) in water solution containing 9.09 weight % ANO was added, with stirring, to VPO catalyst in a weight ratio of 0.22 g solution/1 g catalyst. This catalyst had been previously run under n-butane oxidation conditions to produce maleic anhydride. This used, VPO catalyst sample contained no minor phase $VOPO_4$. After the addition of the ANO solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated to about 200° C. to decompose the oxalate and remove any residual water and then further heated to about 390° C. The catalyst was then tested under the n-butane oxidation conditions. Butane conversion and maleic anhydride yield was as listed in Table 1. Note that the yield is higher than those for the catalysts in Comparative Examples 2-5 and also higher than those for the catalyst in Comparative Example 6.

Examples 11-17

In each of these examples, ammonium niobium oxalate (ANO) in water solution containing 9.09% ANO was added to VPO catalyst in a weight ratio of 0.22 g solution/g catalyst. All of the VPO catalyst in these examples had been run under butane oxidation conditions to produce maleic anhydride for a period of time sufficient to ensure that the minor phase, $VOPO_4$ was reduced to a low level. The addition of the ANO solution to the catalyst was done in a rotary vacuum dryer equipped with spray nozzles. The dryer has plows that mix the catalyst while the ANO solution is sprayed onto the catalyst. Following the addition of the ANO solution, the dryer contents were mixed for about 30 minutes. The dryer was then purged with nitrogen under vacuum, heated to approximately 392° F. to decompose the oxalate and remove residual water, and held at this temperature for about 3 hours before cooling. Portions of the final catalysts were then tested under the n-butane oxidation conditions. Butane conversion and maleic anhydride yield was as listed in Table 1. Note that the yields were higher than those for the catalysts in Comparative Examples 2-5 and also higher than those for the catalyst in Comparative Example 6.

Comparative Example 18

A fresh sample of cobalt promoted VPO catalyst (prepared similarly to the other VPO catalyst used herein but with cobalt added during the catalyst preparation to yield a catalyst containing cobalt at a level of ~0.2 wt. %) was tested under the n-butane oxidation conditions. Butane conversion and maleic anhydride yield was as listed in Table 1. Note that the yield is similar to but slightly lower than those for the catalysts in examples 2-5. Note that the cobalt source for this catalyst was cobalt acetate and it was added during the preparation process (before calcination).

Example 19

A cobalt acetate in water solution containing ~1.1 weight % Co was added, with stirring, to VPO catalyst in a weight ratio of 0.2 g solution/1 g catalyst. The VPO catalyst used had been run under butane oxidation conditions to produce maleic anhydride for a period of time sufficient to ensure that the minor phase, $VOPO_4$ was reduced to a low level. After the addition of the cobalt acetate solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated to about 200° C. and then further heated to about 390° C., producing a catalyst containing ~0.2 weight % Co. The catalyst was then tested under the n-butane oxidation conditions. Butane conversion and maleic anhydride yield was as listed in Table 1. Note that the yield is higher than that for the catalyst in Example 17 and also higher than those for the catalysts in Comparative Examples 2-5.

Example 20

A zinc acetate in water solution containing ~1.7 weight % Zn was added, with stirring, to VPO catalyst. in a weight ratio of 0.22 g solution/1 g catalyst This catalyst had been previously run under butane oxidation conditions to produce maleic anhydride for a period of time sufficient to ensure that the minor phase, $VOPO_4$ was reduced to a low level. After the addition of the zinc acetate solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated to about 200° C. and then further heated to about 390° C., producing a catalyst containing ~0.4 weight % Zn. The catalyst was then tested under the n-butane oxidation conditions. Butane conversion and maleic anhydride yield was as listed in Table 1. Note that the yield is higher than those for the catalysts in Comparative Examples 2-5.

Example 21

A phosphomolybdic acid in water solution containing ~1.7 weight % Mo was added, with stirring, to VPO catalyst in a weight ratio of 0.22 g solution/1 g catalyst. This catalyst had been previously run under butane oxidation conditions to produce maleic anhydride for a period of time sufficient to ensure that the minor phase, $VOPO_4$ was reduced to a low level. After the addition of the phosphomolybdic acid solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated to about 200° C. and then further heated to about 390° C., producing a catalyst containing ~0.4 weight % Mo. The catalyst was then tested under the n-butane oxidation conditions. Butane conversion and maleic anhydride yield was as listed in Table 1. Note that the yield is higher than those for the catalysts in Comparative Examples 2-5.

Example 22

A ferric ammonium citrate in water solution containing ~0.6 weight % Fe was added, with stirring, to VPO catalyst in a weight ratio of 0.22 g solution/1 g catalyst. This catalyst had been previously run under butane oxidation conditions to produce maleic anhydride for a period of time sufficient to ensure that the minor phase, $VOPO_4$ was reduced to a low level. After the addition of the ferric ammonium citrate solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated to about 200 C and then further heated to about 390 C, producing a catalyst containing ~0.13 wt. % Fe. The catalyst was then tested under the n-butane oxidation conditions. Butane conversion and maleic anhydride yield was as listed in Table 1. Note that the yield is higher than those for the catalysts in Comparative Examples 2-5.

Example 23

A titanium (IV) bis(ammonium lactato)dihydroxide in water solution containing ~1.9 wt. To Ti was added, with stirring, to VPO catalyst in a weight ratio of 0.1 g solution/1 g catalyst. This catalyst had been previously run under butane oxidation conditions to produce maleic anhydride for a period of time sufficient to ensure that the minor phase, $VOPO_4$ was reduced to a low level. After the addition of the titanium (IV) bis(ammonium lactato)dihydroxide solution, the catalyst was allowed to air dry overnight in an open dish in a laboratory fume hood. After drying, a portion of the sample was loaded to a 1.5" diameter steel fluidized bed reactor. The catalyst was fluidized with nitrogen and heated to about 200° C. and then further heated to about 390° C., producing a catalyst containing ~0.18 wt. % Ti. The catalyst was then tested under the n-butane oxidation conditions. Butane conversion and maleic anhydride yield was as listed in Table 1. Note that the yield is higher than those for the catalysts in Comparative Examples 2-5.

TABLE 1

| No. | Description | Percent VOPO$_4$ in VPO catalyst before impregnation with solution containing Metal Source Compound | RX Temp ° C. | C4 Conv. % | Maleic Anhydride Yield % |
|---|---|---|---|---|---|
| C2 | VPO catalyst with no metal promotor | | 430 | 89.6 | 56.9 |
| C3 | VPO catalyst with no metal promotor | | 428 | 86.6 | 56.4 |
| C4 | VPO catalyst with no metal promotor | | 440 | 90.1 | 56.2 |
| C5 | VPO catalyst with no metal promotor - used plant sample | | 427 | 87.8 | 54.9 |
| C6 | Nb—VPO catalyst with ANO added during the preparation of the catalyst precursor | | 409 | 86.1 | 58.5 |
| C7 | Nb—VPO catalyst sample prepared by adding ANO to finished VPO catalyst without pre-conditioning of VPO catalyst to lower VOPO$_4$ | 8.6 | 408 | 87.2 | 55.4 |
| C8 | Nb—VPO catalyst sample prepared by adding ANO to finished VPO catalyst without pre-conditioning of VPO catalyst to lower VOPO$_4$ | 24.2 | 422 | 88.8 | 50.3 |
| 9 | Nb—VPO catalyst sample prepared by adding ANO to finished VPO catalyst that had low VOPO$_4$ initially | 2.4 | 416 | 88.7 | 60.5 |
| 10 | Nb—VPO catalyst sample prepared by adding ANO to finished VPO catalyst—used plant sample that had low VOPO$_4$ | 0 | 408 | 87.8 | 61.6 |
| 11 | Nb—VPO catalyst sample prepared by adding ANO to finished VPO catalyst with pre-conditioning of VPO catalyst to lower VOPO$_4$ | 0 | 402 | 87.9 | 61.2 |
| 12 | Nb—VPO catalyst sample prepared by adding ANO to finished VPO catalyst with pre-conditioning of VPO catalyst to lower VOPO$_4$ | 0 | 405 | 88.6 | 61.8 |
| 13 | Nb—VPO catalyst sample prepared by adding ANO to finished VPO catalyst with pre-conditioning of VPO catalyst to lower VOPO$_4$ | 0 | 405 | 87.0 | 62.0 |
| 14 | Nb—VPO catalyst sample prepared by adding ANO to finished VPO catalyst with pre-conditioning of VPO catalyst to lower VOPO$_4$ | 0 | 411 | 88.4 | 61.9 |
| 15 | Nb—VPO catalyst sample prepared by adding ANO to finished VPO catalyst with pre-conditioning of VPO catalyst to lower VOPO$_4$ | 0 | 405 | 89.8 | 62.2 |
| 16 | Nb—VPO catalyst sample prepared by adding ANO to finished VPO catalyst with pre-conditioning of VPO catalyst to lower VOPO$_4$ | <1 | 424 | 89.2 | 59.0 |
| 17 | Nb—VPO catalyst sample prepared by adding ANO to finished VPO catalyst with pre-conditioning of VPO catalyst to lower VOPO$_4$ | 3.6 | 418 | 89.2 | 59.2 |
| C18 | Co—VPO catalyst with cobalt acetate added earlier in the process (Co content ~0.2 wt %) | | 437 | 88.9 | 56.0 |
| 19 | Co—VPO catalyst sample prepared by adding cobalt acetate to finished VPO catalyst with pre-conditioning of VPO catalyst to lower VOPO$_4$ (Co content ~0.2 wt %) | <1 | 428 | 86.2 | 57.7 |
| 20 | Zn—VPO catalyst sample prepared by adding zinc acetate to finished VPO catalyst with pre-conditioning of VPO catalyst to lower VOPO$_4$ (Zn content ~0.4 wt %) | <1 | 433 | 88.3 | 57.7 |
| 21 | Mo—VPO catalyst sample prepared by adding molybdic phosphoric acid to finished VPO catalyst with pre-conditioning of VPO catalyst to lower VOPO$_4$ (Mo content ~0.4 wt %) | <1 | 425 | 88.3 | 58.8 |
| 22 | Fe—VPO catalyst sample prepared by adding iron acetate to finished VPO catalyst with pre-conditioning of VPO catalyst to lower VOPO4 (Fe content ~0.1 wt %) | <1 | 428 | 87.6 | 57.9 |
| 23 | Ti—VPO catalyst sample prepared by adding titanium bis(ammonium lactato) dihydroxide to finished VPO catalyst with pre-conditioning of VPO catalyst to lower VOPO$_4$ (Ti content ~0.2 wt %) | <1 | 434 | 89.5 | 58.6 |

Notes:
1. "RX Temp" is the reactor temperature in ° C.
2. "C4 Conv." is a percentage calculated as (moles of n-butane converted to products and by-product divided by the moles of n-butane fed) × 100.
3. "Maleic Anhydride Yield" is a percentage calculated as (moles of maleic anhydride produced divided by the moles of n-butane fed) × 100.

The data in Table 1 illustrates that improved catalyst for converting butane and oxygen to maleic anhydride can be prepared by adding a metal promoter to a VPO catalyst, wherein the catalyst is promoted with at least one of niobium, cobalt, iron, zinc, molybdenum or titanium. Further, the above data illustrates that the method of addition of the metal promoter is a key to this invention. Specifically adding one of niobium, cobalt, iron, zinc, molybdenum or titanium to the VPO catalyst by impregnation produced a superior catalyst (one that yielded more maleic anhydride) than when niobium was added earlier in the catalyst preparation process. In addition, the data in Table 1 illustrates that improved metal impregnated VPO catalyst are only achieved when the initial VPO catalyst had either no or only a low level of $VOPO_4$ phase present in the catalyst prior to impregnation with the solution comprising a metal source compound of at least one metal selected from the group consisting of niobium, cobalt, iron, zinc, molybdenum or titanium.

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

The claimed invention is:

1. A process for the preparation of a promoted VPO catalyst, wherein the catalyst comprises the mixed oxides of vanadium and phosphorus and wherein the catalyst is promoted with at least one of niobium, cobalt, iron, zinc, molybdenum or titanium, said process comprising the steps of
   (i) preparing a VPO catalyst comprising greater than 80 wt % vanadyl pyrophosphate and less than 5 wt % of vanadyl phosphate,
   (ii) contacting the VPO catalyst with a solution comprising a metal source compound of at least one metal selected from the group consisting of niobium, cobalt, iron, zinc, molybdenum or titanium to form a metal impregnated VPO catalyst, and
   (iii) drying the metal impregnated VPO catalyst to form the promoted VPO catalyst.

2. The process of claim 1, wherein the VPO catalyst comprises greater than 90 wt % vanadyl pyrophosphate and less than 3 wt % of vanadyl phosphate.

3. The process of claim 1 wherein the VPO catalyst has been formed into microsperoidal particles.

4. The process of claim 1 wherein the solution comprising the metal source compound is an organic or aqueous solution comprising a source compound of at least one of niobium, cobalt, iron, zinc, molybdenum or titanium.

5. The process of claim 1, where the solution comprising the metal source compound comprises at least one of ammonium niobium oxalate, cobalt acetate, zinc acetate, phosphomolybdic acid, ferric ammonium citrate, or titanium (IV) bis(ammonium lactato)dihydroxide.

6. The process of claim 1, wherein the metal impregnated VPO catalyst is dried at between 100° C. and 300° C. for 2 to 5 hours.

7. The process of claim 1, wherein the VPO catalyst containing less than 5 wt % of vanadyl phosphate prepared in step (i) is prepared by a preparation method comprising combining a solid VPO catalyst with water, removing the water and collecting the solid by filtration, and then drying the solid filtrate.

8. The process of claim 1, wherein the VPO catalyst containing less than 5 wt % of vanadyl phosphate prepared in step (i) is prepared by a preparation method comprising operating the VPO catalyst under butane oxidation conditions to produce maleic anhydride for between about 1 and about 80 hours.

9. A process for the preparation of a niobium promoted VPO catalyst comprising the mixed oxides of vanadium and phosphorus, said process comprising the steps of
   (i) preparing a VPO catalyst comprising greater than 80 wt % vanadyl pyrophosphate and less than 5 wt % of vanadyl phosphate,
   (ii) contacting the VPO catalyst with a niobium containing solution to form a niobium impregnated VPO catalyst, and
   (iii) drying the niobium impregnated VPO catalyst to form the niobium promoted oxidation catalyst.

10. The process of claim 9, wherein the VPO catalyst comprises greater than 90 wt % vanadyl pyrophosphate and less than 3 wt % of vanadyl phosphate.

11. The process of claim 9 wherein the VPO catalyst has been formed into microsperoidal particles.

12. The process of claim 9 wherein the niobium containing solution is an organic or aqueous solution comprising a niobium source compound.

13. The process of claim 9, where the niobium containing solution comprises ammonium niobium oxalate, $NH_4[NbO(C_2O_4)_2(H_2O)_2].(H_2O)_2$ and water.

14. The process of claim 9, wherein the niobium impregnated VPO catalyst is dried at between 100° C. and 300° C. for 2 to 5 hours.

15. The process of claim 9, wherein the niobium impregnated VPO catalyst is dried at about 200° C. for about 3 hours.

16. The process of claim 9, wherein the VPO catalyst containing less than 5 wt % of vanadyl phosphate prepared in step (i) is prepared by a preparation method comprising combining a solid VPO catalyst with water, removing the water and collecting the solid by filtration, and then drying the solid filtrate.

17. The process of claim 9, wherein the VPO catalyst containing less than 5 wt % of vanadyl phosphate prepared in step (i) is prepared by a preparation method comprising operating the VPO catalyst under butane oxidation conditions to produce maleic anhydride for between about 1 and about 80 hours.

* * * * *